US006719712B2

(12) United States Patent
Zigmont

(10) Patent No.: US 6,719,712 B2
(45) Date of Patent: Apr. 13, 2004

(54) SUPPORT DEVICE FOR SUPPORTING THE BACK, HIPS, UPPER THIGHS AND GROIN AREAS

(76) Inventor: Clifford V. Zigmont, 8039 McLaren Ave., West Hills, CA (US) 91304-3638

( * ) Notice: Subject to any disclaimer, the term of this patent is extended or adjusted under 35 U.S.C. 154(b) by 360 days.

(21) Appl. No.: 09/823,537

(22) Filed: Mar. 30, 2001

(65) Prior Publication Data

US 2001/0047145 A1 Nov. 29, 2001

Related U.S. Application Data

(60) Provisional application No. 60/194,423, filed on Apr. 4, 2000.

(51) Int. Cl.⁷ ................................................... A61F 5/00
(52) U.S. Cl. .................................... 602/19; 2/69
(58) Field of Search .............................. 602/23, 60–63, 602/75; 482/105, 124; 2/44, 69, 466, 467; 450/96, 97, 100, 113, 137, 151, 155, 98–99, 101; 128/869, 873–875

(56) References Cited

U.S. PATENT DOCUMENTS

| | | | | |
|---|---|---|---|---|
| 437,898 A | * | 10/1890 | Thomas ........................ 482/142 |
| 2,531,757 A | * | 11/1950 | Whinery ........................ 602/61 |
| 3,411,500 A | * | 11/1968 | Gatts ............................ 482/124 |
| 4,608,716 A | * | 9/1986 | Brumfield ..................... 2/69 |
| 4,894,867 A | * | 1/1990 | Ceravolo ...................... 2/238 |
| 4,958,386 A | * | 9/1990 | Louis-Jeune ................. 482/124 |
| 5,033,117 A | * | 7/1991 | Fairweather .................. 2/69 |
| 5,176,600 A | * | 1/1993 | Wilkinson .................... 482/124 |
| 5,598,586 A | * | 2/1997 | Munjone ....................... 2/237 |
| 5,652,957 A | * | 8/1997 | Williford ...................... 2/22 |
| 5,659,898 A | * | 8/1997 | Bell, Jr. ........................ 2/69 |
| 5,689,836 A | * | 11/1997 | Fee ................................ 2/465 |
| 5,857,947 A | * | 1/1999 | Dicker et al. ................. 482/124 |
| 5,928,175 A | * | 7/1999 | Tanaka .......................... 602/75 |

\* cited by examiner

Primary Examiner—Michael A. Brown
(74) Attorney, Agent, or Firm—Thomas I. Rozsa; Tony D. Chen

(57) ABSTRACT

A support device that provides support to selected regions of a human body, such as the back, hips, upper thighs and groin areas. The support device comprises an undergarment or bodysuit which is adapted to be disposed against the person's body and extends from the thorax just below the chest) down to the upper thighs. A support belt is positioned at the loin, hips, and abdomen areas of a wearer and secured thereto by a detachable attachment. Two opposite lateral portions extend downwardly from the support belt and secured to the upper thighs of the wearer by detachable attachments. The detachable attachments are adjustable so as to allow the tension against the person's body according to the wearer's preferences.

24 Claims, 4 Drawing Sheets

SUPPORT DEVICE FOR SUPPORTING THE BACK, HIPS, UPPER THIGHS AND GROIN AREAS

This is a non-provisional application of provisional application Ser. No. 60/194,423 filed on Apr. 4, 2000, now pending.

BACKGROUND OF THE INVENTION

1. Field of the Invention

The present invention generally relates to the field of support devices. More particularly, the present invention relates to the field of braces for providing support to the back, hips, upper thighs and groin areas of a person.

2. Description of the Prior Art

Injuries to body parts such as the back, hips, upper thighs and groin are common and result in excruciating pain. Attempts have been made to provide support to the injured back, hips, upper thighs and groin so that a person can lead a normal life without the help of others or support devices, such as a wheelchair or cane.

It is highly desirable to have a very efficient and also very effective design and construction of a support device that is comfortable to wear and provides support to the back, hips, upper thighs and groin areas so that a person wearing the support device can lead a normal life.

SUMMARY OF THE INVENTION

The present invention is a support device that provides support to selected regions of a human body, such as the back, hips, upper thighs and groin areas.

The support device comprises an undergarment or bodysuit which is adapted to be disposed against the person's body and extends from the thorax (just below the chest) down to the upper thighs. Two shoulder straps are provided on top of the undergarment for maintaining the upper portion of the undergarment against the person's body, wherein a respective one shoulder strap encircles a respective one of the person's shoulders. A support belt is positioned at the abdomen area of a wearer and secured to the undergarment by detachable attachment means. Two opposite lateral portions extend downwardly from the support belt and are secured to the undergarment at the locations of the upper thighs of the wearer by detachable attachment means. The detachable attachment means are adjustable so as to allow the tension against the person's body to be adjusted according to the wearer's preferences.

It is an object of the present invention to provide a support device that provides support to the injured back, hips, upper thighs and groin areas of a user and is cosmetically acceptable.

It is an additional object of the present invention to provide a support device that can be worn and removed easily, especially by older people with arthritic or weak hands.

It is a further object of the present invention to provide a support device for providing support to the back, hips, upper thighs, and groin areas that is lightweight and comfortable to wear for extended periods of time.

Further novel features and other objects of the present invention will become apparent from the following detailed description, discussion and the appended claims, taken in conjunction with the drawings.

BRIEF DESCRIPTION OF THE DRAWINGS

Referring particularly to the drawings for the purpose of illustration only and not limitation, there is illustrated.

DETAILED DESCRIPTION OF THE PREFERRED EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention as further defined in the appended claims.

Figure 1:
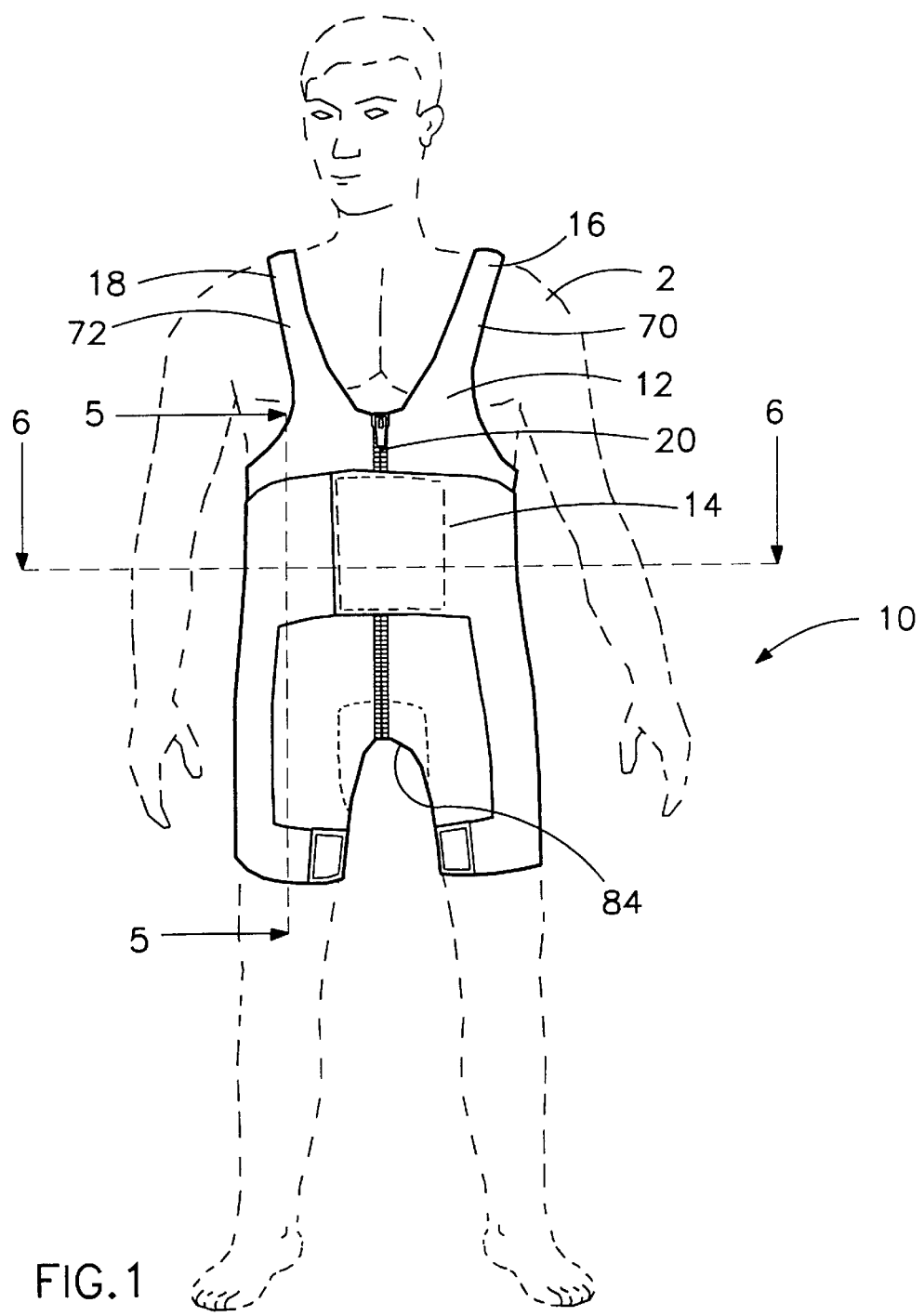
FIG. 1 is a front illustrative view of the present invention support device worn by a user.

Referring to FIG. 1, there is shown at 10 the present invention support device worn by a person 2 (shown in dashed lines) for providing support to the injured back, hips, upper thighs and groin areas. The present invention support device 10 allows the person 2 to engage in everyday activities without excruciating pain while protecting and supporting the injured areas of the body.

Figure 2:
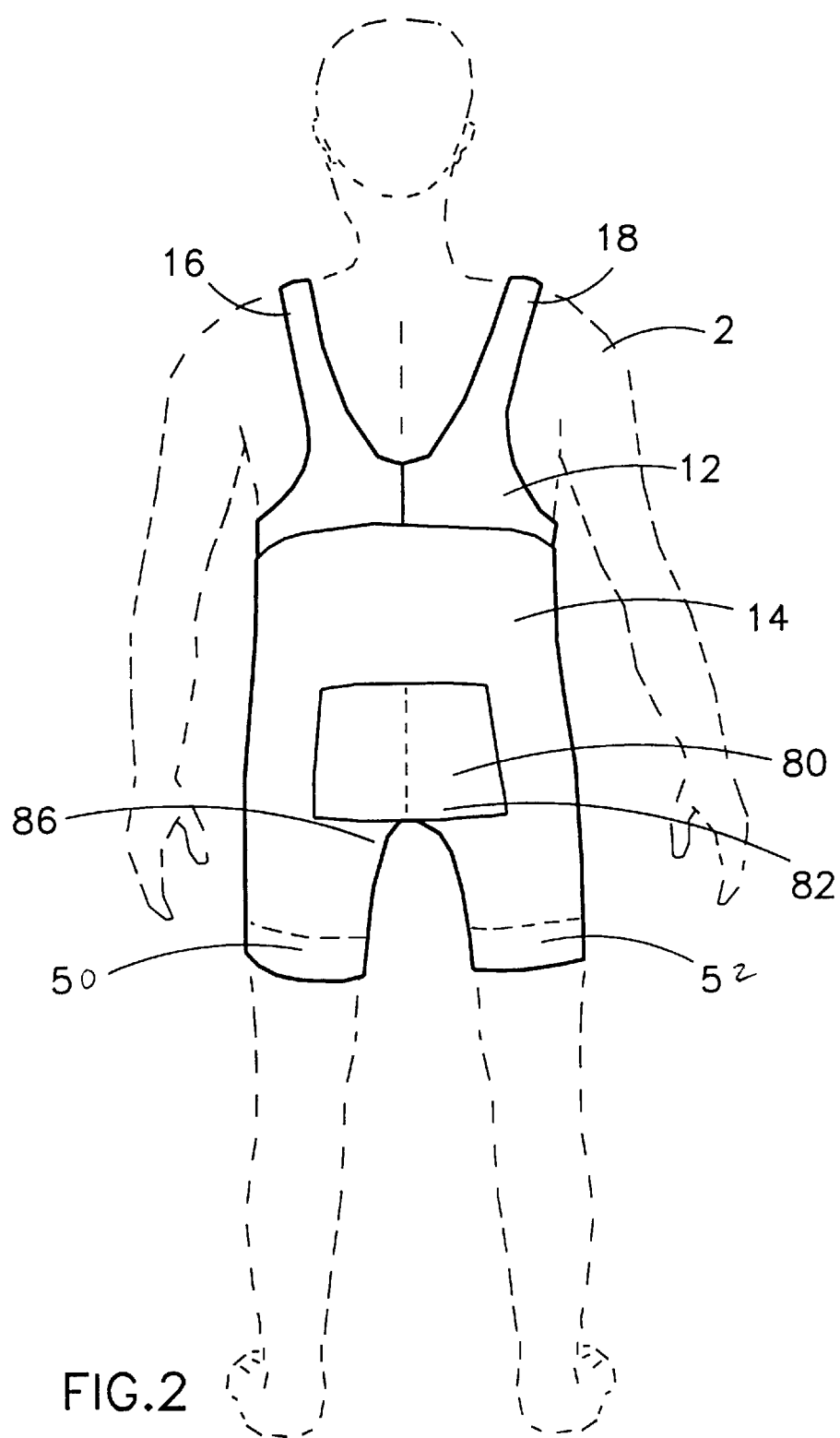
FIG. 2 is a rear illustrative view of the present invention support device worn by the user.

Referring to FIGS. 1 and 2, the support device 10 comprises an undergarment or a partial bodysuit 12 and a support belt 14. The bodysuit 12 has a pair of over-the-shoulder straps 16 and 18 which extends upwardly from the top of the bodysuit 12. The left over-the-shoulder strap 16 encircles the left shoulder while the right over-the-shoulder strap 18 encircles the right shoulder. These two over-the-shoulder straps 16 and 18 further assist in maintaining the bodysuit 12 against the person's body. The over-the-shoulder straps 16 and 18 fit snugly about the shoulders without constricting, gathering, or pinching and allow free movement of the arms.

At the front of the bodysuit 12, there is provided a vertical zipper member 20 which opens and closes the front of the bodysuit 12 for providing easy access to and from the bodysuit 12. The zipper member 20 extends down towards the groin area 84.

The bodysuit 12 further includes a padding 80 for providing comfort to the person wearing the bodysuit 12 and which is sewn onto the interior of the bodysuit 12 and located at the groin area 84, the posterior rugae area 82 and the buttock area 86 of the person 2 wearing the bodysuit 12.

Figure 3:
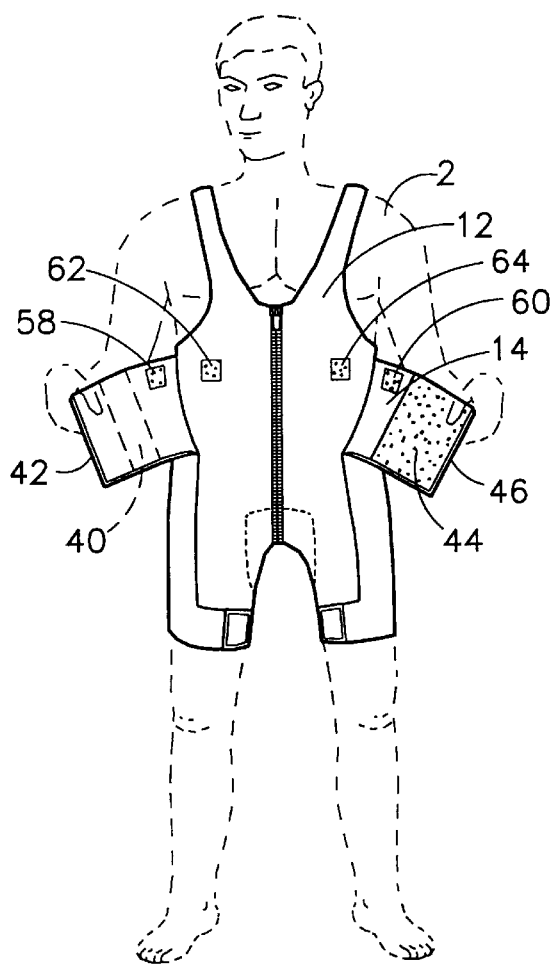
FIG. 3 is an illustrative view of the present invention support device, showing an open support belt unattached together.
Figure 5:
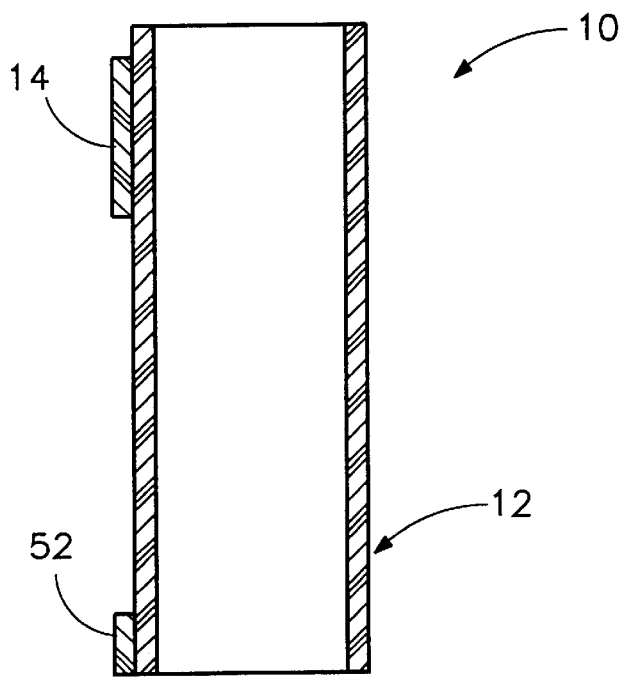
FIG. 5 is a cross-sectional view taken along line 5—5 of FIG. 1.
Figure 6:
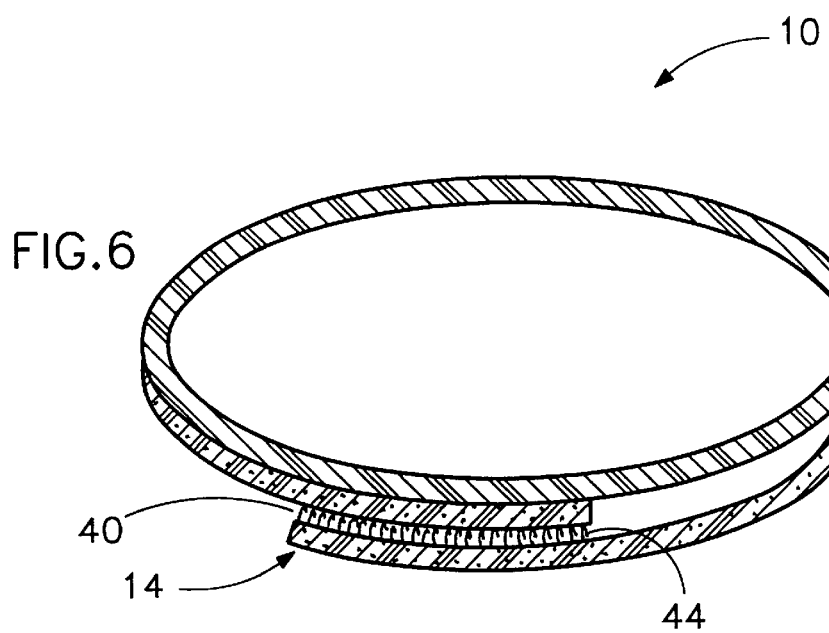
FIG. 6 is a cross-sectional view taken along line 6—6 of FIG. 1.

Referring to FIGS. 3, 5 and 6, there is shown an open support belt 14 which can be secured around the loin, hip and abdomen areas of the person 2 by conventional means. The exterior surface of the support belt 14 has a connecting means 40. The interior surface of the support belt 14 has a mating connecting member 44 which corresponds to the connecting member 40 of the bodysuit 12 for securing the support belt 14 thereto. The support belt 14 has a detachable attachment means for securing the belt 14 thereto. By way of example and illustration only, the detachable attachment means shown comprises a first connecting member 40 attached to the exterior surface at an end portion 42 of the belt 14 by stitching or other suitable means. The detachable attachment means further comprises a mating second connecting member 44 which is attached the interior surface at the other end portion 46 of the belt 14 by stitching or other suitable means. The connecting members 40 and 44 enable the belt 14 to be attached tightly together and around the loin, hip and abdomen areas of the wearer 2 (see FIG. 1). By way of example only, the preferred embodiment of the two connecting members 40 and 44 are mating male hook and female loop type fasteners, commonly known as Velcro®. It will be appreciated that any other suitable connecting members, including buckles, fasteners, snaps, etc. are within the spirit and scope of the present invention.

The support belt 14 further includes connecting members 58 and 60 which are located on the interior of the belt. Mating connecting members 62 and 64 are provided on the front of the bodysuit 12 which respectively mate with the connecting members 58 and 60. These connecting members 58, 60, 62 and 64 support the belt 14 from slipping down on the bodysuit 12.

Figure 4:
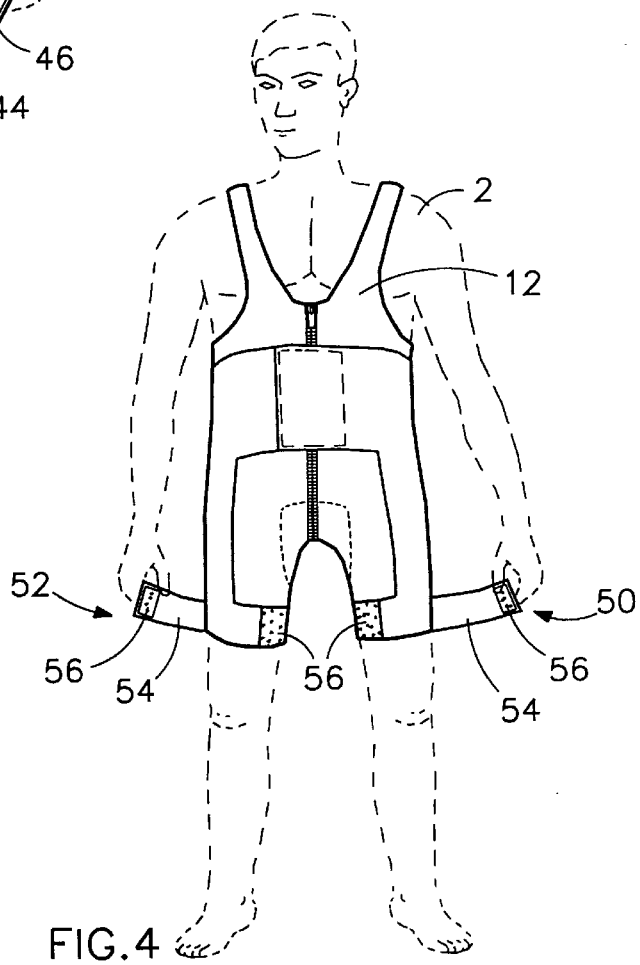
FIG. 4 is an illustrative view of the present invention support device, showing lower lateral portions of the support belt unattached together and located adjacent to the upper thighs of the user.

Referring to FIGS. 4 and 5, there is shown connecting members 50 and 52 which are attached to the thigh portions of the bodysuit 12 by conventional means. Each connecting member has two detachable attachment means 56 which are attached together for holding firmly around and supporting the thigh area of the person 2 when attached. These detachable attachment means 56 are similar to the one just described above, and the description thereof will not be repeated. Each connecting member is secured around the upper thigh of the wearer 2 as shown in FIG. 1. These detachable attachment means are adjustable so as to allow the tension against the person's body according to the wearer's preferences.

The size of the bodysuit 12 varies as needed in order to fit individual users in the manner shown and set forth herein. Therefore, there can be a wide range of possible sizes of undergarment of bodysuit 12.

Construction of the support device 10 is generally achievable by means currently known in the art for the stitching and sewing of apparel. Generally, the entire support device 10 may be made of elastic materials. Materials having greater elasticity should be used. The support belt 14 may be made of the least flexible or even non-flexible material so as to provide a more rigid support. By way of example, the bodysuit 12 can be made of shear neoprene material while the support belt 14 can be made of nylon lycro material. Such materials provide a desirable degree of durability and soil resistance, as well as an acceptable feel and conventional appearance to the support device.

In an alternative embodiment of the present invention support device 10, the over-the-shoulder straps 16 and 18 may have detachable attachment means that are similar to the ones described above, and the description thereof will not be repeated and which can be adjusted according to the wearer's preferences and are located at locations 70 and 72.

It is also within the spirit and scope of the present invention to make this device accommodate female users. For this particular use, it is preferred to have the detachable attachment means on the over-the-shoulder straps 16 and 18 in order to facilitate simple removal of the garment when one is going to the bathroom.

Defined in detail, the present invention is a body support device for supporting a user when worn by the user, comprising: (a) a skintight bodysuit made of a shear neoprene material and having a back side, a front side, a torso portion, a pair of thigh portions extending down from the torso portion for accommodating the user's thighs, and a pair of over-the-shoulder straps extending upwardly from the torso portion to form a top opening for accommodating the user's head and two opposite side openings for accommodating the user's arms; (b) a support belt having a first fastener affixed on one side of the torso portion and a second corresponding mating fastener affixed on the other side of the torso portion, where the first and second fasteners are located between the thorax area and the abdomen area of the user, each fastener having an attachment means for holding firmly around and supporting the back area and the hip area of the user when attached; (c) the each thigh portion having a pair of adjustable fasteners, each adjustable fastener having an attachment means for holding firmly around and supporting the thigh area of the user when attached; and (d) a zipper means located on the front side of the torso portion and extending downwardly to a crotch area of the torso portion for opening or closing the torso portion of the bodysuit.

Defined broadly, the present invention is a body support device for supporting a user when worn by the user, comprising: (a) a non-skintight bodysuit having a back side, a front side, a torso portion, a pair of thigh portions extending down from the torso portion for accommodating the user's thighs, and a pair of over-the-shoulder straps extending upwardly from the torso portion to form a top opening for accommodating the user's head and two opposite side openings for accommodating the user's arms; (b) a support belt having a first fastener affixed on one side of the torso portion and a second corresponding mating fastener affixed on the other side of the torso portion, where the first and second fasteners are located between the thorax area and the abdomen area of the user, each fastener having an attachment means for holding firmly around and supporting the back area and the hip area of the user when attached; (c) the each thigh portion having a pair of adjustable fasteners, each adjustable fastener having an attachment means for holding firmly around and supporting the thigh area of the user when attached; and (d) a zipper means located on the front side of the torso portion and extending downwardly to a crotch area of the torso portion for opening or closing the torso portion of the bodysuit.

Defined more broadly, the present invention is a body support device for supporting a user when worn by the user, comprising: (a) a bodysuit having a front side, a torso portion, at least two thigh portions extending down from the torso portion for accommodating the user's thighs, and at least two over-the-shoulder straps extending upwardly from the torso portion to form a top opening for accommodating the user's head and two opposite side openings for accommodating the user's arms; (b) at least two adjustable fasteners affixed on opposite sides of the torso portion and located between the thorax area and the abdomen area of the user, each adjustable fastener having an attachment means for holding firmly around and supporting the back area and the hip area of the user when attached; (c) the each thigh portion having at least two adjustable fasteners, each adjustable fastener having an attachment means for holding firmly around and supporting the thigh area of the user when attached; and (d) means for opening or closing the torso portion of the bodysuit.

Defined even more broadly, the present invention is a support device to be worn by a user, comprising: (a) a bodysuit having a torso portion and at least two thigh portions; (b) means for holding firmly the torso portion around and supporting the back area and the hip area of the user; and (c) means for holding firmly the at least two thigh portions around and supporting the thigh area of the user.

Of course the present invention is not intended to be restricted to any particular form or arrangement, or any specific embodiment, or any specific use, disclosed herein, since the same may be modified in various particulars or relations without departing from the spirit or scope of the claimed invention hereinabove shown and described of which the apparatus or method shown is intended only for illustration and disclosure of an operative embodiment and not to show all of the various forms or modifications in which this invention might be embodied or operated.

The present invention has been described in considerable detail in order to comply with the patent laws by providing full public disclosure of at least one of its forms. However, such detailed description is not intended in any way to limit the broad features or principles of the present invention, or the scope of the patent to be granted. Therefore, the invention is to be limited only by the scope of the appended claims.

What is claimed is:

1. A body support device for supporting a user when worn by the user, comprising:
   a. a skintight bodysuit made of a shear neoprene material and having, a torso portion with a front side and a back side a pair of thigh portions extending down from the torso portion for accommodating the user's thighs, and a pair of over-the-shoulder straps extending upwardly from the torso portion to form a top opening for accommodating the user's head and two opposite side openings for accommodating the user's arms;
   b. a support belt having a first fastener affixed on one side of said torso portion and a second corresponding mating fastener affixed on the other side of said torso portion, where the first and second fasteners are located between the thorax and abdomen area of the user when attached to the user, each fastener having an attachment means for holding firmly around and supporting the back area and the hip area of said user when attached;
   c. said each thigh portion having a pair of adjustable fasteners, each adjustable fastener having an attachment means for holding firmly around and supporting the thigh area of said user when attached;
   d. a zipper means located on said front side of said torso portion and extending downwardly to a crotch area of said torso portion for opening or closing said torso portion of said bodysuit and
   e. two pairs of attachable and detachable fasteners located on said front side of said torso portion and the interior of said support belt for holding up said support belt.

2. The body support device in accordance with claim 1, wherein said attachment means on each fastener of the support belt is a hook and loop type fastener.

3. The body support device in accordance with claim 1, wherein said crotch area has padding for providing support.

4. The body support device in accordance with claim 1, wherein said torso portion has a buttock area which has padding for providing support.

5. The body support device in accordance with claim 1, wherein said attachment means on each adjustable fastener of the thigh portion is a hook and loop type fastener.

6. A body support device for supporting a user when worn by the user, comprising:
   a. a skintight bodysuit having a torso portion with a front side and a back side, a pair of thigh portions extending down from the torso portion for accommodating the user's thighs, and a pair of over-the-shoulder straps extending upwardly from the torso portion to form a top opening for accommodating the user's head and two opposite side openings for accommodating the user's arms;
   b. a support belt having a first fastener affixed on one side of said torso portion and a second corresponding mating fastener affixed on the other side of said torso portion, where the first and second fasteners are located between the thorax and abdomen areas of the user when attached to the user each fastener having an attachment means for holding firmly around and supporting the back area and the hip area of said user when attached;
   c. said each thigh portion having a pair of adjustable fasteners, each adjustable fastener having an attachment means for holding firmly around and supporting the thigh area of said user when attached;
   d. a zipper means located on said front side of said torso portion and extending downwardly to a crotch area of said torso portion for opening or closing said torso portion of said bodysuit; and
   e. two pairs of attachable and detachable fasteners located on said front side of said torso portion and the interior of said support belt for holding up said support belt.

7. The body support device in accordance with claim 6, wherein said bodysuit is made of a shear neoprene material.

8. The body support device in accordance with claim 6, wherein said attachment means on each fastener of the support belt is a hook and loop type fastener.

9. The body support device in accordance with claim 6, wherein said crotch area has padding for providing support.

10. The body support device in accordance with claim 6, wherein said torso portion has a buttock area which has padding for providing support.

11. The body support device in accordance with claim 6 wherein said attachment means on each adjustable fastener of the thigh portion is a hook and loop type fastener.

12. A body support device for supporting a user when worn by the user, comprising:
   a. a bodysuit having a torso portion with a front side and a back side, at least two thigh portions extending down from the torso portion for accommodating the user's thighs, and at least two over-the-shoulder straps extending upwardly from the torso portion to form a top opening for accommodating the user's head and two opposite side openings for accommodating the user's arms;
   b. at least two adjustable fasteners affixed on opposite sides of said torso portion and located between the thorax and abdomen area of the user when attached to the user, each adjustable fastener having an attachment means for holding firmly around and supporting the back area and the hip area of said user when attached;
   c. said each thigh portion having at least two adjustable fasteners, each adjustable fastener having an attachment means for holding firmly around and supporting the thigh area of said user when attached;
   d. means for opening or closing said torso portion of said bodysuit; and
   e. two pairs of attachable and detachable fasteners located on said front side of said torso portion for holding up said at least two adjustable fasteners affixed on opposite sides of said torso portion.

13. The body support device in accordance with claim 12, wherein said bodysuit is made of a shear neoprene material.

14. The body support device in accordance with claim 12, wherein said attachment means on each fastener of the torso portion of the support belt is a hook and loop type fastener.

15. The body support device in accordance with claim 12, wherein said torso portion has a buttock area which has padding for providing support.

16. The body support device in accordance with claim 12, wherein said means for opening or closing said torso portion includes a zipper means located on said front side of said torso portion and extending downwardly to a crotch area of said torso portion.

17. The body support device in accordance with claim 16, wherein said crotch area has padding for providing support.

18. The body support device in accordance with claim 12 wherein said attachment means on each adjustable fastener of the thigh portion is a hook and loop type fastener.

19. A body support device for supporting a user when worn by the user, comprising:
   a. a skintight bodysuit made of a shear neoprene material and having a torso portion with a front side and a back side a pair of thigh portions extending down from the torso portion for accommodating the user's thighs, and a pair of over-the-shoulder straps extending upwardly from the torso portion to form a top opening for accommodating the user's head and two opposite side openings for accommodating the user's arms;
   b. support belt having a first fastener affixed on one side of said torso portion and a second corresponding mating fastener affixed on the other side of said torso portion, where the first and second fasteners are located between the thorax and abdomen area of the user when attached to the user, each fastener having an attachment means for holding firmly around and supporting the back area and the hip area of said user when attached;
   c. said each thigh portion having a pair of adjustable fasteners, each adjustable fastener having an attachment means for holding firmly around and supporting the thigh area of said user when attached;
   d. a zipper means located on said front side of said torso portion and extending downwardly to a crotch area of said torso portion for opening or closing said torso portion of said bodysuit; and
   e. said crotch area has padding for providing support.

20. A body support device for supporting a user when worn by the user, comprising:
   a. a skintight bodysuit made of a shear neoprene material and having a torso portion with a front side and a back side a pair of thigh portions extending down from the torso portion for accommodating the user's thighs, and a pair of over-the-shoulder straps extending upwardly from the torso portion to form a top opening for accommodating the user's head and two opposite side openings for accommodating the user's arms, said torso portion having a buttock area which has padding for providing support;
   b. a support belt having a first fastener affixed on one side of said torso portion and a second corresponding mating fastener affixed on the other side of said torso portion, where the first and second fasteners are located between the thorax and abdomen area of the user when attached to the user, each fastener having an attachment means for holding firmly around and supporting the back area and the hip area of said user when attached;
   c. said each thigh portion having a pair of adjustable fasteners, each adjustable fastener having an attachment means for holding firmly around and supporting the thigh area of said user when attached; and
   e. a zipper means located on said front side of said torso portion and extending downwardly to a crotch area of said torso portion for opening or closing said torso portion of said bodysuit.

21. A body support device for supporting a user when worn by the user, comprising:
   a. a skintight bodysuit having a torso portion with a front side and a back side, a pair of thigh portions extending down from the torso portion for accommodating the user's thighs, and a pair of over-the-shoulder straps extending upwardly from the torso portion to form a top opening for accommodating the user's head and two opposite side openings for accommodating the user's arms;
   b. a support belt having a first fastener affixed on one side of said torso portion and a second corresponding mating fastener affixed on the other side of said torso portion, where the first and second fasteners are located between the thorax and abdomen area of the user when attached to the user, each fastener having an attachment means for holding firmly around and supporting the back area and the hip area of said user when attached;
   c. said each thigh portion having a pair of adjustable fasteners, each adjustable fastener having an attachment means for holding firmly around and supporting the thigh area of said user when attached;
   d. a zipper means located on said front side of said torso portion and extending downwardly to a crotch area of said torso portion for opening or closing said torso portion of said bodysuit; and
   e. said crotch area has padding for providing support.

22. A body support device for supporting a user when worn by the user, comprising:
   a. a skintight bodysuit having a torso portion with a front side and a back side, a pair of thigh portions extending down from the torso portion for accommodating the user's thighs, and a pair of over-the-shoulder straps extending upwardly from the torso portion to form a top opening for accommodating the user's head and two opposite side openings for accommodating the user's arms, said torso portion having a buttock area which has padding for providing support;
   b. a support belt having a first fastener affixed on one side of said torso portion and a second corresponding mating fastener affixed on the other side of said torso portion, where the first and second fasteners are located between the thorax and abdomen area of the user when attached to the user, each fastener having an attachment means for holding firmly around and supporting the back area and the hip area of said user when attached;
   c. said each thigh portion having a pair of adjustable fasteners, each adjustable fastener having an attachment means for holding firmly around and supporting the thigh area of said user when attached; and
   d. a zipper means located on said front side of said torso portion and extending downwardly to a crotch area of said torso portion for opening or closing said torso portion of said bodysuit.

23. A body support device for supporting a user when worn by the user, comprising:
   a. a bodysuit having a torso portion with a front side and a back side, at least two thigh portions extending down from the torso portion for accommodating the user's thighs, and at least two over-the-shoulder straps extending upwardly from the torso portion to form a top opening for accommodating the user's head and two opposite side openings for accommodating the user's arms;

b. at least two adjustable fasteners affixed on opposite sides of said torso portion and located between the thorax and abdomen area of the user when attached to the user, each adjustable fastener having an attachment means for holding firmly around and supporting the back area and the hip area of said user when attached;

c. said each thigh portion having at least two adjustable fasteners, each adjustable fastener having an attachment means for holding firmly around and supporting the thigh area of said user when attached;

d. means for opening or closing said torso portion of said bodysuit; and e. said torso portion has a crotch area which has padding providing support.

24. A body support device for supporting a user when worn by the user, comprising:

a. a bodysuit having a torso portion with a front side and a back side, at least two thigh portions extending down from the torso portion for accommodating the user's thighs, and at least two over-the-shoulder straps extending upwardly from the torso portion to form a top opening for accommodating the user's head and two opposite side openings for accommodating the user's arms, said torso portion having a buttock area which has padding for providing support;

b. at least two adjustable fasteners affixed on opposite sides of said torso portion and located between the thorax and abdomen area of the user when attached to the user, each adjustable fastener having an attachment means for holding firmly around and supporting the back area and the hip area of said user when attached;

c. said each thigh portion having at least two adjustable fasteners, each adjustable fastener having an attachment means for holding firmly around and supporting the thigh area of said user when attached; and d. means for opening or closing said torso portion of said bodysuit.

* * * * *